(12) United States Patent
Lin et al.

(10) Patent No.: US 9,763,743 B2
(45) Date of Patent: Sep. 19, 2017

(54) APPARATUS AND METHOD FOR TREATING RHINITIS

(71) Applicant: Arrinex, Inc., Redwood City, CA (US)

(72) Inventors: Bryant Lin, Menlo Park, CA (US); David Moosavi, Atherton, CA (US); Mojgan Saadat, Atherton, CA (US); Vahid Saadat, Atherton, CA (US)

(73) Assignee: Arrinex, Inc., Redwood City, CA (US)

( * ) Notice: Subject to any disclaimer, the term of this patent is extended or adjusted under 35 U.S.C. 154(b) by 97 days.

(21) Appl. No.: 14/808,690

(22) Filed: Jul. 24, 2015

(65) Prior Publication Data
US 2016/0045277 A1    Feb. 18, 2016

Related U.S. Application Data

(60) Provisional application No. 62/028,995, filed on Jul. 25, 2014.

(51) Int. Cl.
*A61B 18/02* (2006.01)
*A61B 19/00* (2006.01)
(Continued)

(52) U.S. Cl.
CPC .......... *A61B 19/5202* (2013.01); *A61B 18/02* (2013.01); *A61B 18/082* (2013.01);
(Continued)

(58) Field of Classification Search
CPC ....... A61B 18/02; A61B 18/08; A61B 18/082; A61B 18/14; A61B 18/1485; A61B 18/18;
(Continued)

(56) References Cited

U.S. PATENT DOCUMENTS 5,527,351 A   6/1996  Friedman et al.
5,611,796 A   3/1997  Kamami
(Continued)

FOREIGN PATENT DOCUMENTS

EP    2532300 A2    12/2012
EP    2662027 A1    11/2013
(Continued)

OTHER PUBLICATIONS

Arora, et al., "Cryodestruction of Vidian Nerve Branches", Indian Journal of Otolaryngology, vol. 32, No. 3, Sep. 1980, pp. 80-82.
(Continued)

*Primary Examiner* — Michael Peffley
*Assistant Examiner* — Khadijeh Vahdat
(74) *Attorney, Agent, or Firm* — Kilpatrick, Townsend & Stockton, LLP

(57) ABSTRACT

Devices and methods for treating rhinitis are described where the devices are configured to ablate a single nerve branch or multiple nerve branches of the posterior nasal nerves located within the nasal cavity. A surgical probe may be inserted into the sub-mucosal space of a lateral nasal wall and advanced towards a posterior nasal nerve associated with a middle nasal turbinate or an inferior nasal turbinate into a position proximate to the posterior nasal nerve where neuroablation of the posterior nasal nerve may be performed with the surgical probe. The probe device may utilize a visible light beacon that provides trans-illumination of the sub-mucosal tissue or an expandable structure disposed in the vicinity of the distal end of the probe shaft to enable the surgeon to visualize the sub-mucosal position of the distal end of the surgical probe from inside the nasal cavity using, e.g., an endoscope.

23 Claims, 11 Drawing Sheets

(51) Int. Cl.

| | | |
|---|---|---|
| *A61B 18/08* | (2006.01) | |
| *A61B 18/22* | (2006.01) | |
| *A61N 7/02* | (2006.01) | |
| *A61B 18/14* | (2006.01) | |
| *A61B 18/18* | (2006.01) | |
| *A61B 18/00* | (2006.01) | |
| *A61B 17/00* | (2006.01) | |
| *A61B 34/20* | (2016.01) | |
| *A61B 90/00* | (2016.01) | |

(52) U.S. Cl.
CPC .......... *A61B 18/1485* (2013.01); *A61B 18/22* (2013.01); *A61B 19/5244* (2013.01); *A61N 7/02* (2013.01); *A61B 18/1815* (2013.01); *A61B 2017/00075* (2013.01); *A61B 2017/00106* (2013.01); *A61B 2018/00327* (2013.01); *A61B 2018/00434* (2013.01); *A61B 2018/00577* (2013.01); *A61B 2018/00863* (2013.01); *A61B 2018/00982* (2013.01); *A61B 2019/5206* (2013.01); *A61B 2019/5246* (2013.01); *A61B 2019/5445* (2013.01); *A61B 2034/2055* (2016.02); *A61B 2090/3945* (2016.02)

(58) Field of Classification Search
CPC ................ A61B 18/1815; A61B 18/22; A61B 2017/00075; A61B 2017/00106; A61B 19/5202; A61B 19/5244; A61B 2019/5206; A61B 2019/5246; A61B 2019/5445; A61B 2034/2055; A61B 2090/3945; A61N 7/02
USPC ...................................................... 606/21–27
See application file for complete search history.

(56) References Cited

U.S. PATENT DOCUMENTS

| | | | |
|---|---|---|---|
| 5,733,280 | A | 3/1998 | Avitall |
| 5,899,898 | A | 5/1999 | Arless et al. |
| 5,899,899 | A | 5/1999 | Arless et al. |
| 6,106,518 | A | 8/2000 | Wittenberger et al. |
| 6,210,355 | B1 | 4/2001 | Edwards et al. |
| 6,270,476 | B1 | 8/2001 | Santoianni et al. |
| 6,595,988 | B2 | 7/2003 | Wittenberger et al. |
| 7,104,984 | B2 | 9/2006 | Ryba et al. |
| 7,300,433 | B2 | 11/2007 | Lane et al. |
| 7,418,292 | B2 | 8/2008 | Shafer et al. |
| 7,769,442 | B2 | 8/2010 | Shafer et al. |
| 8,088,127 | B2 | 1/2012 | Mayse et al. |
| 8,142,424 | B2 | 3/2012 | Swanson et al. |
| 8,231,613 | B2 | 7/2012 | Baxter et al. |
| 8,382,746 | B2 | 2/2013 | Williams et al. |
| 8,388,600 | B1 | 3/2013 | Eldredge et al. |
| 8,394,075 | B2 | 3/2013 | Ansarinia et al. |
| 8,425,457 | B2 | 4/2013 | Chang et al. |
| 8,512,324 | B2 | 8/2013 | Abboud et al. |
| 8,676,324 | B2 | 3/2014 | Simon et al. |
| 8,679,104 | B2 | 3/2014 | Abboud et al. |
| 8,715,275 | B2 | 5/2014 | Burger et al. |
| 8,996,137 | B2 | 3/2015 | Wardle et al. |
| 9,050,073 | B2 | 6/2015 | Newell et al. |
| 9,084,592 | B2 | 7/2015 | Wu et al. |
| 9,168,081 | B2 | 10/2015 | Williams et al. |
| 9,265,956 | B2 | 2/2016 | Ackermann et al. |
| 2003/0144659 | A1 | 7/2003 | Edwards et al. |
| 2004/0024412 | A1 | 2/2004 | Clements et al. |
| 2006/0235474 | A1 | 10/2006 | Demarais et al. |
| 2006/0276852 | A1 | 12/2006 | Demarais et al. |
| 2007/0173899 | A1 | 7/2007 | Levin et al. |
| 2007/0265687 | A1 | 11/2007 | Deem et al. |
| 2007/0299433 | A1 | 12/2007 | Williams et al. |
| 2008/0027423 | A1 | 1/2008 | Choi et al. |
| 2008/0119693 | A1 | 5/2008 | Makower et al. |
| 2009/0036948 | A1 | 2/2009 | Levin et al. |
| 2009/0062873 | A1 | 3/2009 | Wu et al. |
| 2009/0076409 | A1 | 3/2009 | Wu et al. |
| 2009/0234345 | A1 | 9/2009 | Hon et al. |
| 2010/0057150 | A1 | 3/2010 | Demarais et al. |
| 2010/0137860 | A1 | 6/2010 | Demarais et al. |
| 2010/0137952 | A1 | 6/2010 | Demarais et al. |
| 2010/0168731 | A1 | 7/2010 | Wu et al. |
| 2010/0168739 | A1 | 7/2010 | Wu et al. |
| 2010/0174282 | A1 | 7/2010 | Demarais et al. |
| 2010/0191112 | A1 | 7/2010 | Demarais et al. |
| 2011/0152855 | A1 | 6/2011 | Mayse et al. |
| 2011/0184402 | A1 | 7/2011 | Baust et al. |
| 2013/0006326 | A1 | 1/2013 | Ackermann et al. |
| 2013/0018366 | A1 | 1/2013 | Wu et al. |
| 2013/0253387 | A1 | 9/2013 | Bonutti et al. |
| 2013/0310822 | A1 | 11/2013 | Mayse et al. |
| 2013/0345700 | A1 | 12/2013 | Hlavka et al. |
| 2014/0186341 | A1 | 7/2014 | Mayse et al. |
| 2014/0228875 | A1 | 8/2014 | Saadat |
| 2014/0236148 | A1 | 8/2014 | Hlavka et al. |
| 2014/0257271 | A1 | 9/2014 | Mayse et al. |
| 2014/0276792 | A1 | 9/2014 | Kaveckis et al. |
| 2014/0277429 | A1 | 9/2014 | Kuzma et al. |
| 2014/0316310 | A1 | 10/2014 | Ackermann et al. |
| 2014/0371812 | A1 | 12/2014 | Ackermann et al. |
| 2015/0031946 | A1 | 1/2015 | Saadat et al. |
| 2015/0080870 | A1 | 3/2015 | Wittenberger |
| 2015/0126986 | A1 | 5/2015 | Kelly et al. |
| 2015/0164571 | A1* | 6/2015 | Saadat ................... A61B 17/24 600/109 |
| 2015/0196345 | A1 | 7/2015 | Newell et al. |
| 2015/0238754 | A1 | 8/2015 | Loudin et al. |
| 2015/0313661 | A1 | 11/2015 | Wu et al. |
| 2016/0022992 | A1 | 1/2016 | Franke et al. |
| 2016/0045277 | A1 | 2/2016 | Lin et al. |
| 2016/0114163 | A1 | 4/2016 | Louidin et al. |
| 2016/0114172 | A1 | 4/2016 | Louidin et al. |
| 2016/0121118 | A1 | 5/2016 | Franke et al. |
| 2016/0158548 | A1 | 6/2016 | Ackermann et al. |
| 2016/0317794 | A1 | 11/2016 | Saadat |
| 2016/0354135 | A1* | 12/2016 | Saadat ................... A61B 17/24 |
| 2016/0354136 | A1* | 12/2016 | Saadat ................... A61B 17/24 |

FOREIGN PATENT DOCUMENTS

| | | |
|---|---|---|
| EP | 2662046 A1 | 11/2013 |
| EP | 2662116 A1 | 11/2013 |
| WO | 2008051918 A2 | 5/2008 |
| WO | 2012027641 A3 | 5/2012 |
| WO | 2013035192 A1 | 3/2013 |
| WO | 2013173481 A2 | 11/2013 |

OTHER PUBLICATIONS

Bumsted, "Cryotherapy for Chronic Vasomotor Rhinitis: Technique and Patient Selection for Improved Results", Laryngoscope, vol. 94, Apr. 1984, pp. 539-544.

Girdhar-Gopal, "An Assessment of Postganglionic Cryoneurolysls for Managing Vasomotor Rhinitis", American Journal of Rhinology, vol. 8, No. 4,, Jul.-Aug. 1994, pp. 157-164.

Golhar, et al., "The effect of Cryodestruction of Vidian Nasal Branches on Nasal Mucus Flow in Vasomotor Rhinitis", Indian Journal of Otolaryngology, vol. 33, No. 1, Mar. 1981, pp. 12-14.

Goode, "A Liquid Nitrogen Turbinate Probe for Hypertrophic Rhinitis", Arch Otolaryngol., vol. 103, 1977, p. 431.

Mehra, et al., "Cryosurgery in Vasomotor Rhinitis—An Analysis of 156 Patients", Indian Journal of Otolaryngology, vol. 42, No. 3, Sep. 1990, pp. 95-98.

Ozenberger, "Cryosurgery for the Treatment of Chronic Rhinitis", Laryngoscope, vol. 83, No. 4, 1973, pp. 508-516.

Ozenberger, "Cryosurgery in Chronic Rhinitis", The Laryngoscope, vol. 80, No. 5, May 1970, pp. 723-734.

Principato, "Chronic Vasomotor Rhinitis: Cryogenic and Other Surgical Modes of Treatment", The Laryngoscope, vol. 89, 1979, pp. 619-638.

(56) References Cited

OTHER PUBLICATIONS

Rao, "Cryosurgery on Inferior turbinate hypertrophy under topical anaesthesia—is it boon in electricity deprived places", National Journal of Otorhinolaryngology and Head & Neck Surgery, vol. 1 (10), No. 1, Apr. 2013, pp. 7-9.

Strome, "A long-term assessment of cryotherapy for treating vasomotor instability", vol. 69, No. 12, http://apps.webofknowledge.com.laneproxy.stanford.edu/OutboundServic...marked_list_candidates=1&excludeEventConfig=ExcludeIfFromFullRecPage, Dec. 1990, pp. 839-842.

Terao, et al., "Cryosurgery on Postganglionic Fibers (Posterior Nasal Branches) of the Pterygopalatine Ganglion for Vasomotor Rhinitis", Acta Otolaryngol., vol. 96, 1983, pp. 139-148.

\* cited by examiner

View A-A

View A-A

View C-C

View D-D

APPARATUS AND METHOD FOR TREATING RHINITIS

CROSS-REFERENCE TO RELATED APPLICATIONS

This application claims priority to U.S. Provisional Patent Application No. 62/028,995 filed Jul. 25, 2014, which is incorporated herein by reference in its entirety.

FIELD OF THE INVENTION

The present invention relates to cryosurgical probes and their methods of use. More particularly, the present invention relates to cryosurgical probes which are configured to be advanced into a nasal cavity for treating conditions such as rhinitis.

BACKGROUND OF THE INVENTION

The major symptoms of allergic or non-allergic chronic rhinitis are sneezing, rhinorrhea, and night time coughing which are brought about by mucosal swelling, hyper-responsiveness of the sensory nerves, and an increased number and augmented responses of secretory cells in the interior turbinates, respectively. In particular, chronic severe nasal obstruction resulting from remodeling of submucosal tissues of the inferior turbinates due to dilation of the venous sinuses or fibrosis can interfere with the quality of life (QOL).

One strategy is the surgical treatment of chronic rhinitis; that is to physically eliminate the tissue of the inferior turbinate. Removal or ablation of the mucosal tissue including the surface epithelial layer has the disadvantage of postoperative complications such as crusting and an increased infection rate. Cauterization of the surface epithelia of the inferior turbinate using electrocautery, cryosurgery, or laser yields only short-term benefits to nasal breathing. Submucosal diathermy or cryosurgery also shows only a short-term effect. Turbinectomy is thought to have the greatest effect on nasal obstruction, and slight improvement in some rhinitis patients but it is accompanied by severe adverse effects such as bleeding, crusting, and nasal dryness.

Golding-Wood, who recommended cutting the parasympathetic nerve fibers in the vidian canal to decrease the parasympathetic tone to the nasal mucosa, introduced a different approach for the treatment of hypersecretion in 1961. Various approaches to the vidian canal were subsequently developed, and the method was widely employed in the 1970s. However, the original technique was abandoned at the beginning of the 1980s because of its irreversible complications such as dry eyes.

The pterygoid canal carries both parasympathetic and sympathetic fibers, namely the vidian nerve, to the sphenopalatine ganglion. Subsequently, these autonomic fibers, which relay in the sphenopalatine ganglion, reach the nasal mucosa through the sphenopalatine foramen as the posterior nasal nerve. Resection of the posterior nasal nerve has the effect of both parasympathetic and sympathetic resection in the nasal mucosa, similar to vidian neurectomy. In addition, this procedure, in which somatic afferent innervation to the nasal mucosa is also interrupted, can be expected to reduce the hypersensitivity and axon reflexes of the nasal mucosa. The posterior nasal nerve, which follows the sphenopalatine artery and vein, arises within the sphenopalatine foramen and can be easily identified. Furthermore, selective interruption of the posterior nasal nerves has no complications, like those of vidian neurectomy, since the secretomotor supply to the lacrimal gland and the somatosensory supply to the palate are intact, and overpenetration of the pterygoid canal does not occur.

Posterior nasal neurectomy, initially developed by Kikawada in 1998 and later modified by Kawamura and Kubo, is a novel alternative method in which neural bundles are selectively cut or cauterized from the sphenopalatine foramen. Autonomic and sensory nerve fibers that pass through the foramen anatomically branch into the inferior turbinate and are distributed around the mucosal layer. Therefore, selective neurectomy at this point enables physicians to theoretically avoid surgical complications such as inhibition of lacrimal secretion.

SUMMARY OF THE INVENTION

There are three nerve bundles innervating the superior, middle and inferior turbinates. The posterior, superior lateral nasal branches off of the maxillary nerve (v2) innervate the middle and superior turbinates. A branch of the greater palatine nerve innervates the inferior turbinate. Ablating these nerves leads to a decrease in or interruption of parasympathetic nerve signals that contribute to rhinorrhea in patients with allergic or vasomotor rhinitis. The devices and methods described herein are configured for ablating one or more of these three branches to reduce or eliminate rhinitis.

The following is the description of the embodiments that achieve the objectives of ablating the Posterior Nasal Nerves (PNN). Any of the ablation devices can be used to ablate a single nerve branch or multiple nerve branches.

In accordance with one aspect of this invention is a method for treating rhinitis comprising inserting the distal end of a surgical probe into the sub-mucosal space of a lateral nasal wall, then advancing the distal end towards a posterior nasal nerve associated with a middle nasal turbinate or an inferior nasal turbinate into a position proximate to the posterior nasal nerve, then performing neuroablation of the posterior nasal nerve with the surgical probe.

One embodiment of the surgical probe may be configured for sub-mucosal neuroablation of a posterior nasal nerve associated with a middle nasal turbinate, or an inferior nasal turbinate and may generally comprise a surgical probe shaft comprising an elongated hollow structure with a distal end and a proximal end, wherein the surgical probe shaft is sized for insertion into and advancement within a sub-mucosal space of a lateral nasal wall from within a nasal cavity; a handle coupled to the proximal end; a neuroablation agent delivery mechanism disposed on the distal end; and an optical beacon disposed in a vicinity of the distal end, wherein the optical beacon provides an indication of a position of the distal end within the nasal cavity when visualized.

In use, one embodiment for a method of treating rhinitis may generally comprise inserting the distal end of the surgical probe into the sub-mucosal space of a lateral nasal wall located within the nasal cavity, the surgical probe comprising the surgical probe shaft with the distal end and the proximal end, the handle coupled to the proximal end, the neuroablation agent delivery mechanism disposed on the distal end, and the optical beacon disposed in the vicinity of the distal end; visualizing a cul de sac defined by a tail of a middle nasal turbinate, lateral wall, and inferior nasal turbinate within the nasal cavity; advancing the distal end towards the cul de sac and into proximity of the posterior nasal nerve associated with a middle nasal turbinate or an inferior nasal turbinate while visually tracking a position of the distal end by trans-illumination of the optical beacon through mucosa; and performing neuroablation of the posterior nasal nerve.

The surgical probe comprises a probe shaft with a distal end and a proximal end. A surgical hand piece is disposed in the vicinity of the proximal end, and a neuroablation implement is disposed in the vicinity of the distal end. The surgical probe shaft may be configured with an endoscopic visualization aid disposed in the vicinity of the distal end that allows the surgeon to determine the sub-mucosal position of the distal end by endoscopic observation of the lateral nasal wall from inside of the associated nasal cavity.

In one embodiment of the method the endoscopic visualization aid is a visible light beacon that provides trans-illumination of the sub-mucosal tissue allowing the surgeon to visualize the sub-mucosal position of the distal end of the surgical probe from inside the associated nasal cavity using an endoscope. The light beacon may be configured to emit light that is within the green segment of the visible optical spectrum. The green segment of the visible optical spectrum is absorbed strongly by hemoglobin and absorbed weakly by connective tissues. The target posterior nasal nerve(s) is co-sheathed with an associated artery and vein, The arrangement of having the nerve, artery and vein that are related to the same anatomical function is common in mammalian anatomy. Since the green light is strongly absorbed by both the arterial and venous hemoglobin, the visible trans-illumination from the light beacon will be dimmed when the light beacon is positioned immediately proximate to the sheath comprising the target posterior nasal nerve, due to absorption of the green light by the blood flowing through the associated artery and vein. This provides a means for locating the target posterior nasal nerve by locating, its associated artery and vein.

The endoscopic visualization aid may comprise an expandable structure disposed in the vicinity of the distal end of the surgical probe shaft. The expandable structure is configured with a user operated inflation and deflation device. The surgical probe may he inserted into the sub-mucosal space in with the expandable structure in an un-expanded state, then advanced towards the target posterior nasal nerve. When the surgeon needs to determine the position of the distal end of the surgical probe, the expandable structure is expanded by the surgeon displacing the overlying mucosal tissue, which is visible by endoscopic observation from within the nasal cavity providing the surgeon an indication of the location of the distal end of the surgical. The surgical probe comprises a device for the user to inflate and deflate the expandable structure, which is disposed on the surgical hand piece. The expandable structure may also be used to help advance the distal end of the surgical probe by using the expandable structure to create a blunt dissection through the surgical plane defined by the bone of the nasal wall and the overlying mucosa.

The neuroablation device may comprise a tissue heating mechanism, or a tissue freezing mechanism, or may comprise the sub-mucosal delivery of a neurolytic solution to the vicinity immediately proximate to the target posterior nasal nerve. Regardless of the neuroablation mechanism, the method is conceived such that collateral damage to adjacent vital structures is avoided by limiting the zone of therapeutic effect to the immediate vicinity of the target posterior nasal nerve. The minimization of collateral damage is facilitated by the visualization aided accurate placement of the distal neuroablation implement in the immediate proximity of the target posterior nasal nerve, and precise control of the neuroablation parameters.

In one embodiment of the method a surgical probe is used that is configured for neuroablation by tissue heating comprising at least one radio frequency (RF) electrode disposed in the vicinity of the distal end of the surgical probe shaft. The RF electrode(s) is connected to one pole of an RF energy generator. Alternatively, at least two electrodes may be disposed in the vicinity of the distal end with at least one electrode connected to one pole of an RF energy generator, and at least one additional electrode connected to the second pole of the RF energy generator. The RF energy generator may reside within the surgical hand piece, and the wire(s) connecting the RF electrode(s) to the RF energy generator may reside within the surgical probe shaft. The RF energy generator and the RF electrodes may be configured to heat tissue by. e.g., Ohmic resistance effect, in a manner intended to limit the volume tissue that is heated to the target zone that is immediately proximate to the posterior nasal nerve. The surgical probe may be configured for user selection of the neuroablation operating parameters including RF power, RF current, target tissue temperature, and heating time.

In another embodiment of the method a surgical probe is used that is configured for heating comprising an ultrasonic energy emitting transducer connected to an ultrasonic energy generator. The ultrasonic energy transducer is configured to heat tissue in a manner that limits the heating effect to the volume of tissue immediately proximate to the target posterior nasal nerve. The surgical probe may be configured for user selection of neuroablation parameters including ultrasonic. energy frequency, power, target tissue temperature, and heating time. The ultrasonic generator may be disposed within the hand piece, and the wire(s) connecting the ultrasonic transducer to the ultrasonic energy transducer may reside within the surgical probe shaft. The surgical probe may be configured where the ultrasonic transducer provides Doppler blood flow sensing in addition to tissue heating. Ultrasonic doppler blood flow sensing can be used to sense arterial or venous blood flow that is in close proximity to the ultrasonic transducer, which allows the surgeon to avoid damage to an artery or a vein with the surgical probe, or to find a target posterior nasal nerve by sensing the blood flow through the artery or vein associated with the posterior nasal nerve.

In an alternative embodiment of the method a surgical probe is used that is configured for tissue heating comprising an optical energy tissue heating mechanism. An optical energy generator may be disposed within the surgical hand piece, and an optical fiber may transmit the optical energy from the optical energy venerator to the distal end of the surgical probe shaft into the proximate distal tissue. The optical energy generator may be a laser diode. The surgical probe may be configured with user selectable neuroablation parameters including optical power, optical wavelength(s), pulse width and frequency, and time of heating. The surgical probe may be configured with more than one optical energy generator where one optical energy generator is configured for tissue heating, and a second optical energy generator is configured for providing visible light for a distal optical beacon that functions as an endoscopic visualization aid by means of trans-illumination of the nasal mucosa, allowing the distal end of the surgical probe to be visualized from inside the nasal cavity by trans-illumination through the overlying mucosal tissue. A single optical transmission fiber may be configured for tissue heating, and for providing a distal optical beacon.

One embodiment of the method comprises the use of a surgical probe configured for tissue freezing. The surgical probe comprises a liquid cryogen evaporation chamber disposed in the vicinity of the distal end, and a liquid cryogen reservoir disposed within the surgical hand piece. A liquid cryogen conduit is disposed within the surgical probe shah between the liquid cryogen evaporation chamber and the liquid cryogen reservoir. The liquid cryogen evaporation chamber may comprises a rigid metallic structure, or may comprise an expandable structure. The expandable structure may be configured as a liquid cryogen evaporation chamber, and as an endoscopic visualization aid. The expandable structure may be configured to expand in response to liquid cryogen evaporation, and may be configured for expansion independently of liquid cryogen evaporation. The surgical probe may be inserted into the sub-mucosal space with the expandable structure in an un-expanded state, then advanced towards the target posterior nasal nerve. When the surgeon needs to determine the position of the distal end of the surgical probe, the expandable structure is expanded by the surgeon displacing the overlying mucosal tissue, which is visible by endoscopic observation from within the nasal cavity providing the surgeon an indication of the location of the distal end of the surgical probe Shaft. The surgical probe comprises a mechanism for the user to inflate and deflate the expandable structure, which is disposed on the surgical hand piece. The expandable structure may also be used to help advance the distal end of the surgical probe by using, the expandable structure to create a blunt dissection through the surgical plane defined by the bone of the nasal wall and the overlying mucosa. A surgical probe comprising cryogen liquid evaporation chamber that is a rigid metallic structure may also be configured with an expandable structure configured for inflation and deflation by the user which is configured as an endoscopic visualization aid, and for blunt dissection as described above. Alternatively to the cryogen evaporation chamber comprising a rigid metallic structure, a tissue freezing element may comprise, e.g., a Joule-Thompson effect tissue freezing mechanism, and be within the scope of this invention.

In one embodiment of the method a surgical probe is used that is configured for neuroablation of target posterior nasal nerve(s) by sub-mucosal delivery of a neurolytic solution immediately proximate to the target posterior nasal nerve(s). The neurolytic solution may be a neurotoxic agent, a parasympatholytic agent, or a sclerosing agent. A neurotoxic agent may be botulinum toxin, β-Bunarotoxin, tetnus toxin, α-Latrotoxin or another neurotoxin. A sympatholytic agent may be Guanethidine, Guanacline, Bretylium Tosylate, or another sympatholytic agent. A sclerosing agent may be ethanol, phenol, a hypertonic solution or another sclerosing agent. The surgical probe comprises a reservoir of neurolytic solution disposed upon the surgical hand piece. A liquid, conduit is disposed within the surgical probe shaft between the reservoir of neurolytic solution and the distal end of the surgical probe shaft A mechanism to inject the neurolytic solution into the sub-mucosal tissue immediately proximate to the target posterior nasal nerve in a controlled manner is also disposed on the surgical hand piece. The liquid neuroablation reservoir and the means to control injection may comprise a syringe filled with a neurolytic solution. An endoscopic visualization aid is disposed in the vicinity of the distal end of the surgical probe shaft.

The insertion of the distal end of the surgical probe into the sub-mucosal space of a lateral nasal wall may be done at a location that is anterior to the middle nasal turbinate or the inferior nasal turbinate. The anterior insertion location is more accessible than locations that are more posterior for both the endoscopic imaging and surgical probe manipulation. After insertion of the distal end of the surgical probe into the sub-mucosal space, the distal end of the surgical probe is advanced towards the target posterior nasal nerve along the surgical plane defined by the bone of the lateral nasal wall and the overlying mucosal tissue. The surgical probe is advanced under one or both of the middle nasal turbinate and inferior nasal turbinate.

The endoscopic visualization aid is used to provide the surgeon with the position of the distal end of the surgical probe shaft during the advancement. An alternative location for insertion of the distal end of the surgical probe shaft into the sub-mucosal space is in between the middle turbinate and the inferior turbinate. This location is closer to the target posterior nasal nerve(s) therefore there is a reduced length of blunt dissection during probe advancement towards the target posterior nasal nerve(s), however, the access to the sub-mucosal space is more difficult, and may require surgical lateralization of one or both of the middle nasal turbinate and inferior nasal turbinate, The distal end of the surgical probe shaft may also be inserted into the sub-mucosal space in the immediate vicinity of the cul de sac defined by the tail of the middle turbinate, the lateral wall and in the inferior nasal turbinate.

The embodiments of the method that utilize tissue heating or tissue freezing as a neuroablation means may further comprise protecting the superficial mucosa proximate to the target posterior nasal nerve(s) from injury as a result of the sub-mucosal neuroablation. In the embodiments of the method that utilize tissue heating as a neuroablation means, the superficial mucosa may be cooled during the neuroablation procedure to prevent the temperature of the superficial mucosal from exceeding a tissue heating injury threshold. In the embodiments of the method that utilize tissue freezing as a neuroablation means, the superficial mucosa may be warmed during the neuroablation procedure to prevent the temperature of the superficial mucosa from exceeding a freezing tissue injury threshold. The superficial mucosa may be warmed or cooled using warm or cold saline irrigation of the surface of the superficial mucosa. Also a balloon with a circulating warm or cold liquid may be pressed against the lateral nasal wall proximate to the target posterior nasal nerve during the neuroablation procedure to protect the superficial mucosa from thermal injury. Protecting the superficial mucosa from thermal injury resulting from sub-mucosal neuroablation will reduce crusting, pain and inflammation following the procedure, speed the recovery period, and prevent infection of the nasal mucosa.

In another aspect of this invention is a surgical probe configured for sub-mucosal neuroablation of a posterior nasal nerve associated with a middle nasal turbinate or an inferior nasal turbinate. The surgical probe comprises a surgical probe shaft that is an elongated hollow structure with a distal end and proximal end. A surgical hand piece is disposed on the proximal end of the surgical probe shaft. A neuroablation implement is disposed at the distal end of the surgical probe shaft. An endoscopic visualization aid is disposed on the surgical probe shaft in the vicinity of the distal end. The surgical probe is configured for the distal end to be inserted into the sub-mucosal space of a lateral nasal wall from inside of a nasal cavity, and to be advanced to a position proximate to a target posterior nasal nerve along the surgical plane defined by the bone of the lateral nasal wall and the overlying mucosa, while visualizing the advancement from within the associated nasal cavity using an endoscope and the endoscopic visualization aid. The endoscopic visualization aid may be a visible light beacon comprising visible light. The visible light may be configured to be in the green segment of the visible light spectrum. The brightness of the visible light beacon. may be adjustable, and the adjustment means may be disposed on the surgical hand piece.

Alternatively, the endoscopic visualization aid may comprise an expandable structure that is configured for inflation and deflation by the surgeon. The expandable structure is configured to displace the overlying mucosal tissue in a manner that is visually detectable by endoscopic observation of the surface of the lateral nasal mucosa from within the nasal cavity. The endoscopic visualization aid may also comprise a bulbous structure that is non-expandable, that is configured to be visually detectable by endoscopic observation. The neuroablation implement may comprise a tissue heating mechanism, a tissue freezing mechanism or the distal delivery of a neurolytic solution proximate to a target nasal nerve.

The tissue heating mechanism may comprise the delivery of optical energy proximate to the posterior nasal nerve. The optical energy source may be disposed within the surgical hand piece, which may comprise at least one laser diode. The optical energy may be delivered to the tissue proximate to the posterior nasal nerve by an optical transmission fiber disposed between the optical energy source and the distal end of the surgical probe shaft. The optical energy may be substantially in the red and/or near infrared part of the optical spectrum, with an optical power level between approximately, e.g., 0.2 watts and 2.0 watts. The surgical probe's endoscopic visualization aid may be in the form of an optical beacon, and may comprise light substantially in the green part of the optical spectrum. The surgical hand piece may be configured with two optical energy sources; one configured for tissue heating, and a second configured for use with the optical beacon. Optical energy from both optical energy sources may be delivered to the distal end of the surgical probe shaft by a common optical transmission fiber. The optical transmission fiber may comprise an optical transmission fiber bundle.

The tissue heating mechanism may comprise at least one electrode disposed on the distal end connected to a pole of a radio frequency (RIP) energy generator. The energy generator may be disposed within the surgical hand piece. The tissue heating mechanism may comprise at least one ultrasonic energy emitting transducer disposed on the distal end of the surgical probe shaft connected to an ultrasonic energy generator. The ultrasonic energy generator may be disposed within the surgical hand piece. The tissue heating means may comprise a microwave energy emitting antenna disposed on the distal end connected to a microwave energy generator. The microwave generator may be disposed within the surgical hand piece. The tissue heating mechanism may also comprise a hot contact surface disposed at the distal end. The hot contact surface may be resistively heated by connection to an electrical power source. The electrical power source may be disposed within the surgical hand piece.

The surgical probe may be configured with a tissue freezing mechanism comprising a liquid cryogen evaporation chamber disposed on the distal end of the surgical probe shaft. A reservoir comprising liquid cryogen may be disposed within the surgical hand piece, as well as a user activated liquid cryogen control valve. At least one liquid cryogen conduit is disposed between the liquid cryogen evaporation chamber and the liquid cryogen reservoir and liquid cryogen flow control valve disposed within the surgical probe shaft. The liquid cryogen evaporation chamber may comprise a hollow metallic chamber that is substantially rigid. Alternatively, the liquid cryogen evaporation chamber may comprise an expandable structure that is configured for expansion in response to liquid cryogen evaporation, The expandable structure may be configured as a tissue freezing mechanism and an endoscopic visualization aid. The expandable structure may be configured for user operated inflation and deflation by a mechanism in addition to expansion in response to liquid cryogen evaporation.

The surgical probe may be configured to deliver a neurolytic solution into the sub-mucosal tissue immediately proximate to the target posterior nasal nerve. The surgical probe may be configured with a reservoir comprising a neurolytic solution. The reservoir may he disposed upon the surgical hand piece. The surgical hand piece may he configured with a means for distal delivery of the neurolytic solution in a highly controlled manner. The neurolytic solution may comprise a neurotoxic agent, a sympatholytic agent, or a sclerosing agent. A neurotoxic agent may be botulinum toxin, β-Bunarotoxin, tetnus toxin, α-Latrotoxin or another neurotoxin A sympatholytic agent may be Guanethidine, Guanacline, Bretylium Tosylate, or another sympatholytic agent. A sclerosing agent may be ethanol, phenol, a hypertonic solution or another sclerosing agent.

DETAILED DESCRIPTION OF THE INVENTION

Figure 1:
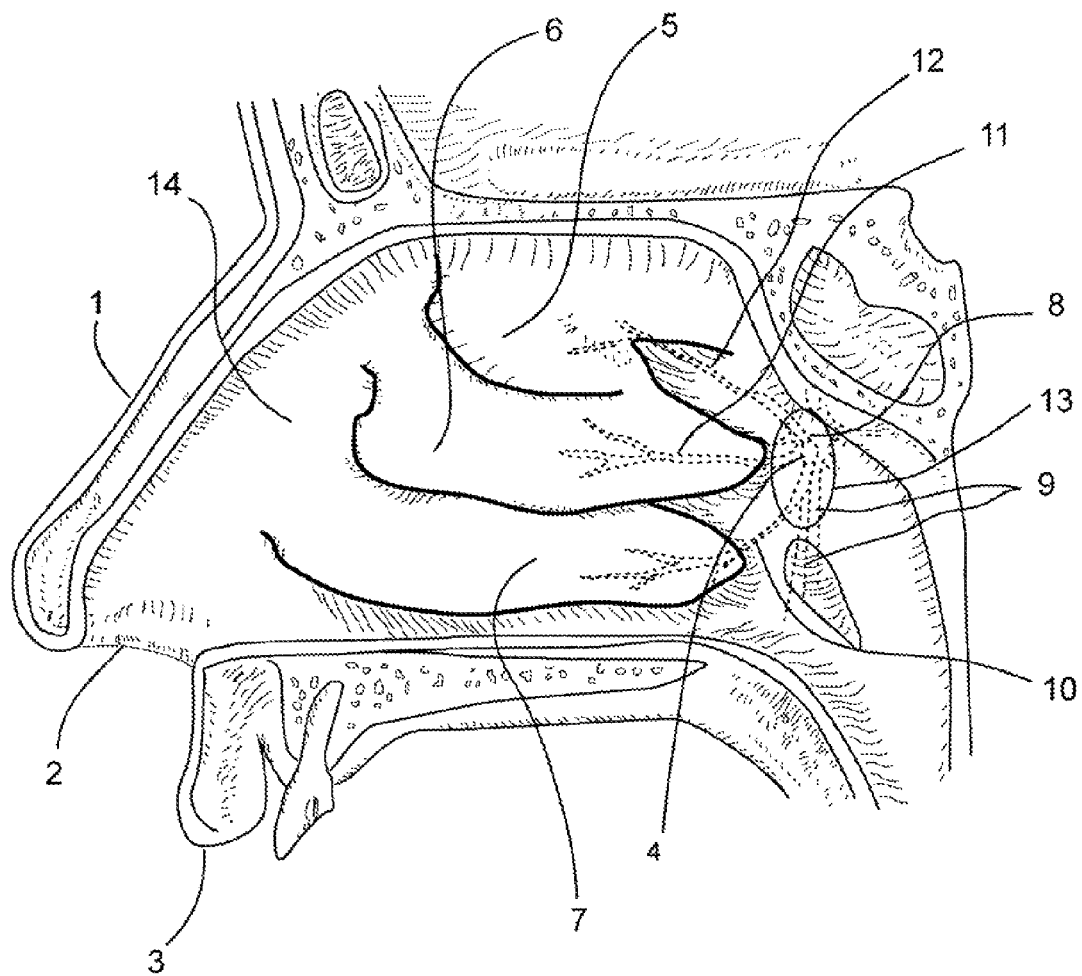
FIG. 1 is an internal lateral view of the nasal canal showing the nasal anatomy relevant to this invention, and the targeted region of the lateral nasal wall for neuroablation of posterior nasal nerve function.

FIG. 1 depicts an internal view of the nasal cavity showing the nasal anatomy relevant to this invention. Shown for orientation is the lateral nasal wall 14, the nose 1, nostril 2, upper lip 3, sphenopalatine foramen 4, superior nasal turbinate 5, middle nasal turbinate 6, inferior nasal turbinate 7, postnasal nerve 8, greater palatine nerve 9, posterior nerve inferior lateral branch 10, posterior nerve middle lateral branch 11, posterior nerve superior inferior nasal branch 12, and cul de sac 13 defined by the tail of the middle nasal turbinate 6, lateral wall 14, and the inferior turbinate 7. Posterior nasal nerve 8 is within a sheath comprising the sphenopalatine artery and vein, not shown. Posterior nasal nerve branches 10, 11, and 12 are co-sheathed with the corresponding branches of the sphenopalatine artery and vein. Posterior nasal. nerve 8 rises through the sphenopalatine foramen 4 along with the sphenopalatine artery and vein and remain, along with its branches 10, 11, and 12 between approximately 1 mm to 4 mm below the surface of the nasal mucosa. The posterior nasal nerve 8 or its branches 10, 11 and 12 are targets for sub-mucosal functional neuroablation for the treatment of rhinitis according to this invention.

Figure 2A:
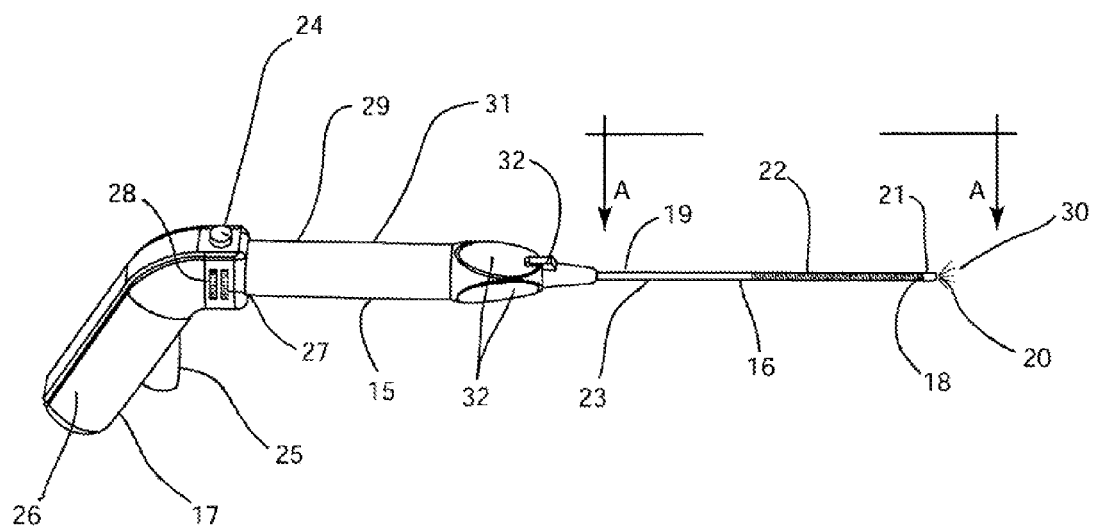
FIGS. 2A and 2B are schematic illustrations of a surgical probe configured for sub-mucosal neuroablation of a posterior nasal nerve comprising an optical beacon that functions as an endoscopic visualization aid.

FIG. 2A is a schematic illustration of sub-mucosal neuroablation probe 15. Sub-mucosal neuroablation probe 15 is a generic representation of multiple embodiments of this invention. Sub-mucosal neuroablation probe 15 comprises surgical probe shaft 16, and surgical hand piece 17. Surgical probe. shaft 16 is a hollow elongated structure with a distal end 18, and a proximal end 19. Surgical hand piece 17 is disposed at the proximal end 19 of surgical probe shaft 16. Surgical probe shaft 16 comprises rigid segment 23, which is proximal to flexible segment 22. A neuroablation implement 21 is disposed near the distal end of flexible segment 22, as shown. Associated with the neuroablation implement 21 is optical beacon 20. Neuroablation implement 21 may be configured for sub-mucosal neuroablation by at least one of the following neuroablation mechanisms: neuroablation by tissue freezing mechanism, neuroablation by tissue heating and coagulation mechanism, or neuroablation by sub-mucosal delivery of a neurolytic solution. The neurolytic solution may comprise a neurotoxic agent, a sympatholytic agent, or a sclerosing agent. A neurotoxic agent may be botulinum toxin, β-Bunarotoxin, tetnus toxin, α-Latrotoxin or another neurotoxin. A sympatholytic agent may be Guanethidine, Guanacline, Bretylium Tosylate, or another sympatholytic agent. A sclerosing agent may be ethanol, phenol, a hypertonic solution or another sclerosing agent For embodiments of the invention that use tissue freezing as a neuroablation means, neuroablation implement 21 represents a liquid cryogen evaporation chamber, or a gas expansion chamber configured with a Joule-Thompson mechanism. For embodiments that utilize tissue heating and coagulation as a neuroablation mechanism, implement 21 may represent a radiofrequency (RF) energy heating, element, a microwave energy heating element, an ultrasonic energy heating element, optical energy heating element, or resistive heating element. For embodiments of the invention that utilize sub-mucosal delivery of a neurolytic solution, neuroablation implement 21 may comprise a distal aperture of a fluid channel configured for sub-mucosal delivery of a neurolytic solution.

Surgical hand piece 17 comprises pistol grip 26, optical beacon brightness control knob 24, neuroablation actuator trigger 25, neuroablation parameter(1) control knob 27, neuroablation parameter(2) control knob 28, finger grip 29, finger barrel 31, and neuroablation actuator button 32. Surgical hand piece 17 may be configured to be held like a piston by the surgeon using pistol grip 26, or the surgeon may hold surgical hand piece 17 like a writing utensil using finger grips 29, with finger grip barrel 31 residing between the thumb and index finger of the surgeon Surgical hand piece 17 may be configured with neuroablation actuators comprising pistol trigger neuroablation actuator 25, which may be used to actuate and terminate a neuroablation when the surgeon holds the surgical probe 15 using pistol grip 19. Neuroablation actuator button 32 may be used to actuate and terminate a neuroablation when the surgeon holds surgical probe 1 S by finger grips 29.

For embodiments of the invention that utilize tissue freezing as a neuroablation mechanism, surgical hand piece 17 may comprise a liquid cryogen reservoir, not shown, that may be supplied from the factory with liquid cryogen and configured for a single patient use. Alternatively, surgical hand piece 17 may be configured for use with a user replaceable liquid cryogen reservoir in the form of a cartridge. Liquid cryogen cartridges are readily commercially available from many sources. Neuroablation actuator trigger 25, and neuroablation actuator button 32 may be configured as cryogen control actuators.

Neuroablation parameter(1) control knob 27 and neuroablation parameter(2) control knob ma be configured to control at least one of the following neuroablation parameter: Cryogen flow rate, cryogen flow time, tissue set point temperature, evaporation set point temperature, or an active re-warming temperature or power.

For embodiments of the invention that utilize tissue heating and coagulation as a neuroablation mechanism, hand piece 17 may comprise an energy generator disposed within, which may be an RF energy generator, a microwave energy generator, an ultrasonic energy generator, an optical energy generator, or an energy generator configured for resistive heating. Neuroablation actuator trigger 25 and neuroablation actuator button 32 may be configured to turn an energy generator on and off, Neuroablation parameter(1) control knob 27, and neuroablation parameter(2) control knob 28 may be configured to control at least one of the following neuroablation parameters: a set point tissue temperature, a heating power, a heating: current, a heating voltage, or a heating time.

There are embodiments were neuroablation actuator trigger 25, neuroablation actuator button 32, neuroablation parameter(1) control knob 27, or neuroablation parameter(2) control knob 28 may be absent. Embodiments that utilize sub-mucosal delivery of a neurolytic solution may not utilize these features.

Optical beacon 20 is configured as an endoscopic visualization aid. Optical beacon 20 provides trans-illumination of the nasal mucosa and provides the surgeon with an endoscopic determination of the exact position of neuroablation implement 21 within the sub-mucosal space by endoscopic imaging of the surface of the mucosa of the lateral nasal wall. Surgical hand piece 17 comprises a light source, not shown, configured for supplying distal optical beacon 20 light via an optical transmission fiber disposed within probe shaft 16 between the light source and the distal optical beacon 20, Optical beacon brightness control knob 24 is configured for controlling the brightness of optical beacon 24. The light source may be configured to emit light that is in the green segment of the visible optical spectrum, which is strongly absorbed by hemoglobin, and weakly absorbed by connective tissue. The optical beacon is configured for trans-illumination of the nasal mucosa, which is endoscopically observed from inside of the nasal cavity, which provides a visual mechanism for locating the neuroablation implement 21. When optical beacon 20 is placed in close proximity to the sphenopalatine artery and vein, which are co-sheathed the target posterior nasal nerve, the hemoglobin within the artery and vein strongly absorb the green light from optical beacon 20 resulting, in an observable dimming of the mucosal trans-illumination.

Figure 2B:
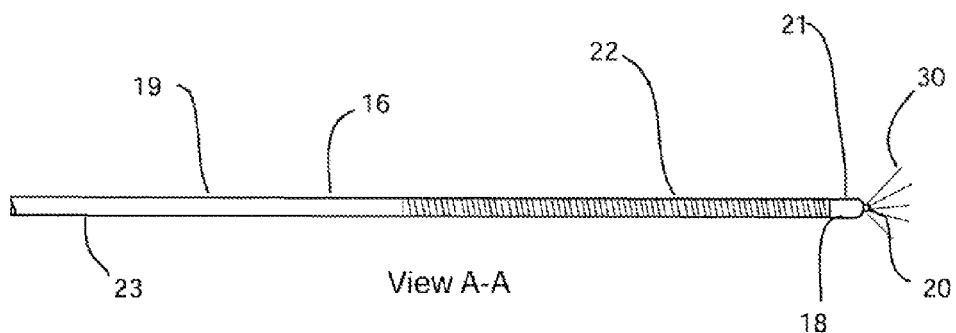

FIG. 2B is a schematic illustration of surgical probe shaft 16 taken at section "A-A" from FIG. 2A. Surgical probe shaft 16 is between approximately, e.g., 1 mm and 4 mm in diameter, and between approximately, e.g., 4 cm and 10 cm in length. The rigid segment 23 of surgical probe shaft 16 may be fabricated from a surgical grade stainless steel hypodermic tube, or may alternatively be fabricated from a polymeric extrusion. Flexible segment 22 of probe shaft 16 may be fabricated as a flat metal wire coil, or may be fabricated as a metal wire reinforced polymeric extrusion. Flexible segment 22 is configured to provide sufficient column strength to transverse the mucosa during insertion into the sub-mucosal space, and to be flexible enough to follow the surgical plane defined by the bone of the lateral nasal wall and the mucosa as the distal end 18 is advanced towards the target posterior nasal nerve 8, or its branches 10, 11, or 12 Flexible segment 22 may have a higher flexibility in one lateral direction than another to facilitate "steering" through the sub-mucosal space. The length of flexible segment 23 may be approximately 30% to 70% of the length of surgical probe shaft 16. Those skilled in the art of flexible surgical probe shafts are familiar with mechanisms for producing a surgical probe shaft with the characteristics disclosed here within; therefore no further description is warranted.

Figure 3A:
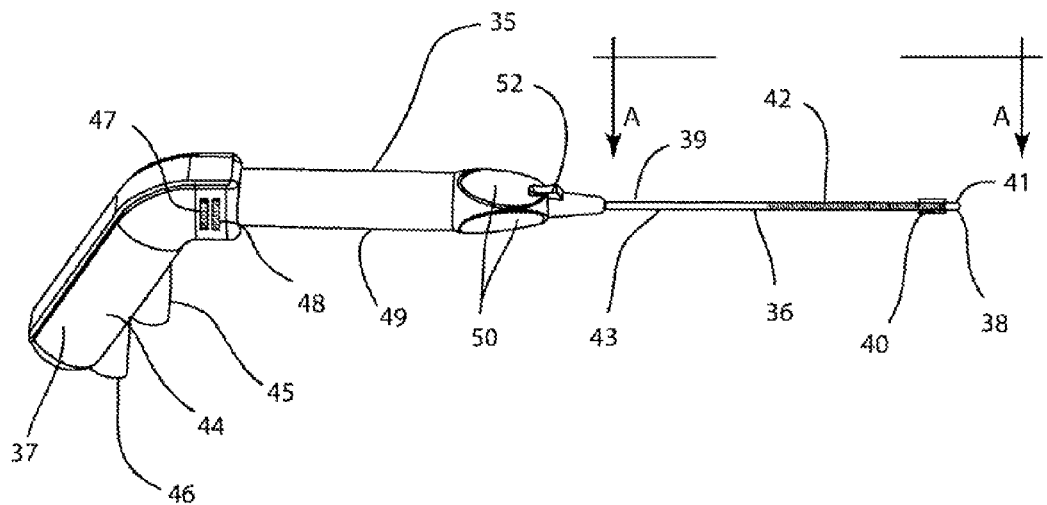
FIG. 3A is a schematic illustration of a surgical probe configured for sub-mucosal neuroablation of a posterior nasal nerve comprising an expandable structure configured as an endoscopic visualization aid with the expandable structure in its unexpanded state.

FIG. 3A is a schematic illustration of sub-mucosal neuroablation probe 35. Sub-mucosal neuroablation probe 35 is an alternative embodiment to sub-mucosal. neuroablation probe 15 and uses an expandable structure 40 as an endoscopic visualization aid in lieu of an optical beacon. Sub-mucosal neuroablation probe 35 comprises surgical probe shaft 36, and surgical band piece 37. Surgical probe shaft 36 is a hollow elongated structure with a distal end 38, and a proximal end 39. Surgical hand piece 37 is disposed at the proximal end 39 of surgical probe shaft 36. Surgical probe shaft 36 comprises rigid segment 43, which is proximal to flexible segment 42, A neuroablation implement 41 is disposed near the distal end of flexible segment 42, as shown. Associated with the neuroablation implement 41 is expandable structure 40. Neuroablation implement 41 may be configured for sub-mucosal neuroablation by at least one of the following neuroablation means: neuroablation by tissue freezing mechanism, neuroablation by tissue heating and coagulation mechanism, or neuroablation by sub-mucosal delivery of a neurolytic solution. The neurolytic agent may be a neurotoxin, a sympatholytic, or a sclerosing agent. For embodiments of the invention that use tissue freezing as a neuroablation mechanism, neuroablation implement 41 represents a liquid cryogen evaporation chamber, or a gas expansion chamber configured with a Joule-Thompson mechanism. For embodiments of the invention that utilize tissue heating and coagulation as a neuroablation mechanism, implement 41 may represent a radiofrequency (RF) energy heating element, a microwave energy heating element, an ultrasonic energy heating element, and optical energy heating element or resistive heating element. For embodiments of the invention that utilize sub-mucosal delivery of a neurolytic solution, neuroablation implement 41 may comprise a distal aperture of a fluid channel configured for sub-mucosal delivery of a neurolytic solution.

Surgical hand piece 37 comprises pistol grip 44, neuroablation actuator trigger 45, expandable structure inflation/deflation control lever 46, neuroablation parameter(1) control knob 47, neuroablation parameter(2) control knob 48, finger grips 50, finger grip barrel 49, and neuroablation actuator button 52. Surgical hand piece 37 may be configured to be held like a piston by the surgeon using pistol grip 44, or the surgeon may hold surgical hand piece 37 like a writing utensil using finger grips 50, with finger grip barrel 49 residing between the thumb and index finger of the surgeon. Surgical hand piece 37 may be configured with neuroablation actuators comprising pistol trigger neuroablation actuator 45, which may be used to actuate and terminate a neuroablation when the surgeon holds the surgical probe 35 using pistol grip 44. Neuroablation actuator button 52 ma be used to actuate and terminate a neuroablation when the surgeon holds surgical probe 35 by finger grips 50.

For embodiments of the invention that utilize tissue freezing as a neuroablation mechanism, surgical hand piece 37 may comprise a liquid cryogen reservoir, not shown, that may be supplied from the factory with liquid cryogen and configured for a single patient use. Alternatively, surgical hand piece 37 may be configured for use with a user replaceable liquid cryogen reservoir in the form of a cartridge. Liquid cryogen cartridges are readily commercially available from many sources. Neuroablation actuator trigger 45 and neuroablation actuator button may be configured as cryogen control actuators. Neuroablation parameter(1) control knob 47 and neuroablation parameter(2) control knob 48 may be configured to control at least one of the following neuroablation parameters: Cryogen flow rate, cryogen flow time, tissue set point temperature, evaporation set point temperature, or an active re-warming temperature or power.

For embodiments that utilize tissue heating and coagulation as a neuroablation mechanism, hand piece 37 may comprise an energy generator disposed within, which may be an RF energy generator, a microwave energy generator, an ultrasonic energy generator, an optical energy generator, or an energy generator configured for resistive heating. Neuroablation actuator trigger 45 and neuroablation actuator button 52 may be configured to turn an energy generator on and off. Neuroablation parameter(1) control knob 47, and neuroablation parameter(2) control knoll 48 may be configured to control at least one of the following neuroablation parameters: A set point tissue temperature, a heating power, a heating current, a heating voltage, or a heating time.

There are embodiments where neuroablation actuator trigger 45, neuroablation actuator button 52, neuroablation parameter(1) control knob 47, or neuroablation parameter(2) control knob 48 may absent. Embodiments that utilize sub-mucosal delivery of a neurolytic solution may not utilize these features.

Figure 3B:
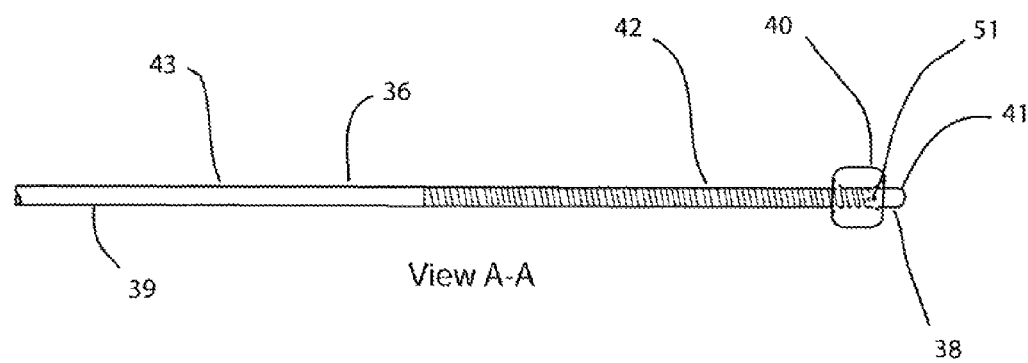
FIG. 3B is a schematic illustration of a surgical probe configured for sub-mucosal neuroablation of a posterior nasal nerve comprising an expandable structure configured as an endoscopic visualization aid with the expandable structure in its expanded state.

Expandable structure 40 is disposed in the vicinity of distal end 38, and is proximal to neuroablation implement 41. Expandable structure 40 may be fabricated from an elastomeric material such as silicone rubber, or may be fabricated from a substantially non-elastic material such as PET or polyethylene. During insertion of surgical probe shaft 36 into the sub-mucosal space, expandable structure 40 is in an un-expanded state. To visually identify the location of the distal end 38 of probe shaft 36 by endoscopic observation of the lateral nasal wall 14, expandable structure 40 is expanded as depicted in FIG. 3B. The expanded diameter of expandable structure 40 is between approximately, e.g., 4 mm and 8 mm, and the axial length of expandable structure 40 is between approximately, e.g., 4 mm and 8 mm. The configuration and construction of expandable structure 40 is substantially similar to an occlusion balloon, which is a common surgical instrument. Those skilled in the an of surgical instruments and occlusion balloons are familiar with the means for incorporating and expandable structure as described above, therefore, no further description is warranted. The interior of expandable structure 40 is in fluidic communication with a fluid reservoir, which may be disposed within surgical hand piece 37. Expandable structure 40 is expanded by insertion of fluid from the fluid reservoir into the interior of expandable structure 40 under pressure through fluid port 51. The fluid is removed from the interior of expandable structure 40 under suction, to return expandable structure 40 to its un-expanded state. Inflation/deflation control lever 46 is configured to pressurize and de-pressurize the fluid reservoir within surgical hand piece 37. Alternatively, expandable structure 40 may be configured to be in fluidic communication with a fluid filled syringe, which may be used for inflation and deflation of expandable structure 40.

Figure 4A:
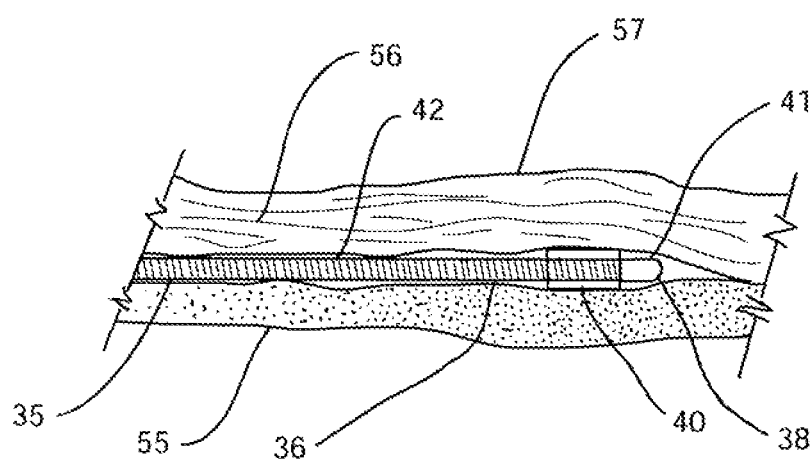
FIG. 4A is a cross sectional schematic illustration of the distal end of a surgical probe comprising an expandable structure configured as an expandable structure in a sub-mucosal position in the surgical plane defined by the bone of the lateral nasal wall and the overlying mucosal, with the expandable structure in its unexpanded state.
Figure 4B:
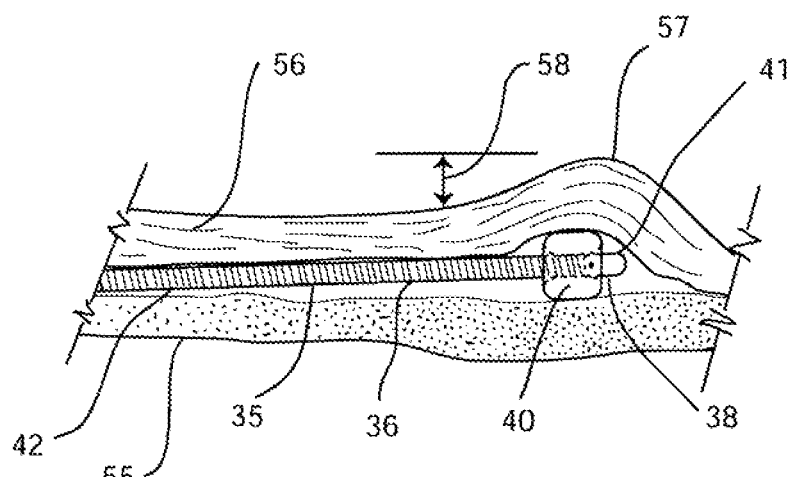
FIG. 4B is a cross sectional schematic illustration of the distal end of a surgical probe comprising an expandable structure configured in a sub-mucosal position in the surgical plane defined by the bone of the lateral nasal wall and the overlying mucosal with the expandable structure in its expanded state.

FIG. 4A and FIG. 4B are schematic cross sectional illustrations depicting the distal end 38 of surgical probe shaft 36 inserted into the surgical plane between the bone of the lateral nasal wall and the nasal mucosa. FIG. 4A depicts expandable structure 40 in its unexpanded state. FIG. 4B depicts expandable structure 40 in its expanded state, showing the resulting lateral displacement 58 of the nasal mucosal surface 57. The lateral displacement 58 is visually detectable by endoscopic observation, which provides the surgeon with the location of distal end 38 of surgical probe shaft 36 relative to the nasal anatomy.

Figure 5A:
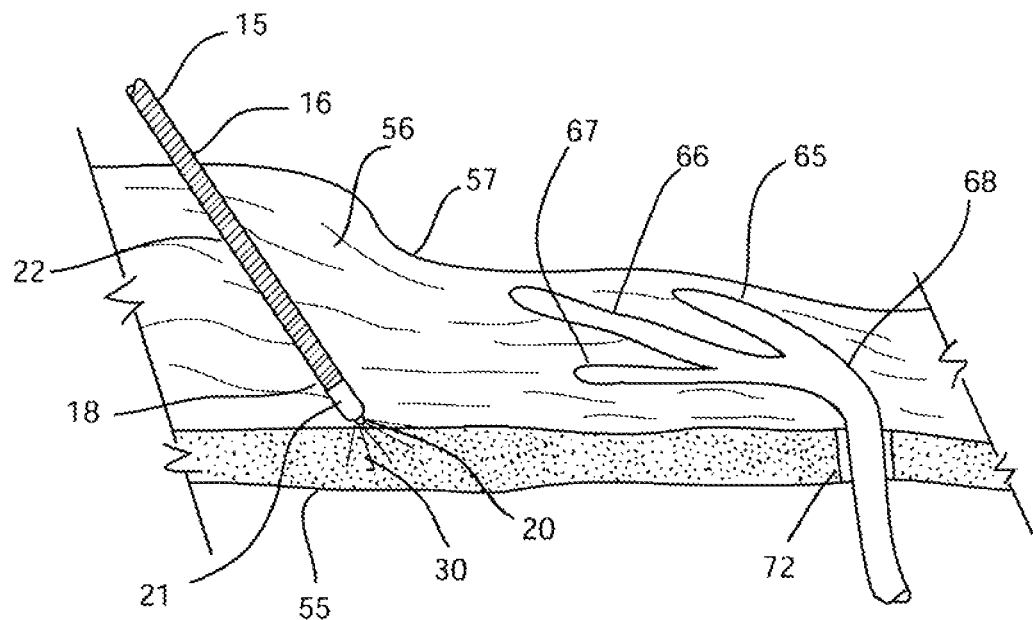
FIG. 5A is a cross section schematic illustration of the surgical probe shall with the distal end partially inserted into the sub mucosal space.
Figure 5B:
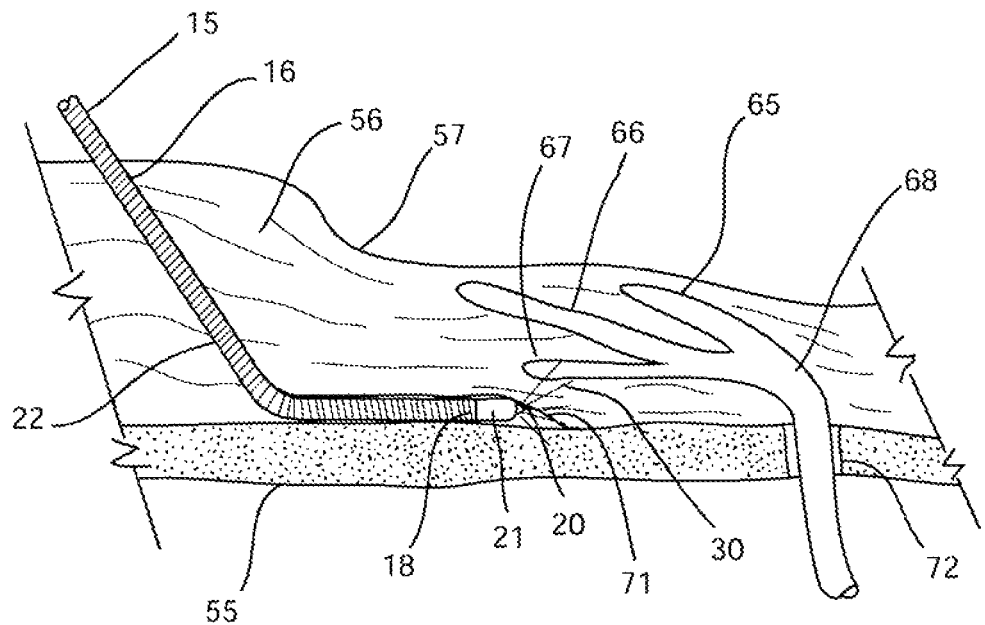
FIG. 5B is a cross section schematic illustration of the surgical probe shaft being advanced towards the target posterior nasal nerve along the surgical plane defined by the bone of the lateral nasal wall and the overlying mucosa.
Figure 5C:
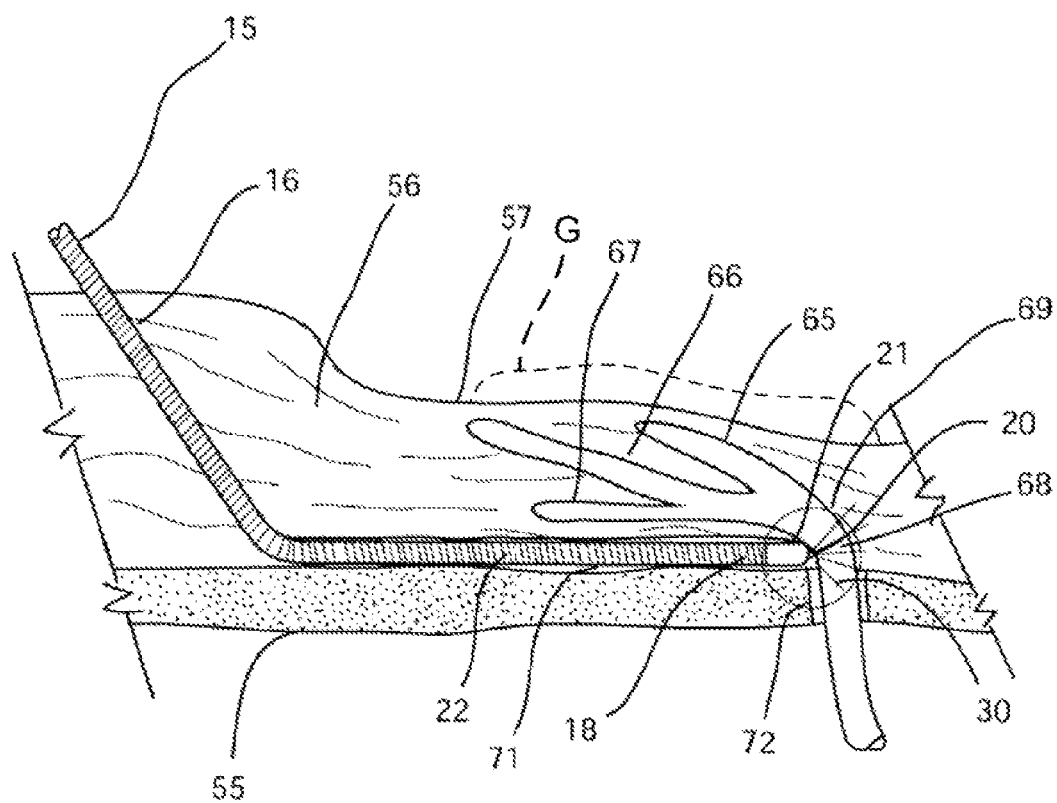
FIG. 5C is a cross sectional illustration of the surgical probe shaft with its distal end positioned proximate to the target posterior nasal nerve.

FIG. 5A, FIG. 5B and FIG. 5C are cross sectional illustrations depicting the serial insertion of the distal end 18 of surgical probe shaft 16 into the sub-mucosal space 56 (FIG. 5A), and the advancement, of distal end 18 of surgical probe shaft 16 towards the target posterior nasal nerve 8 (FIG. 5B), and the positioning of neuroablation implement 21 into position for neuroablation immediately proximate to target posterior nasal nerve 8 (FIG. 5C). FIG. 5A depicts distal end 18 inserted into the nasal mucosal from an insertion point that is anterior to the sphenopalatine foramen 4 and posterior nasal nerve 8. FIG. 5A depicts the insertion of surgical probe shaft 16 to the point where neuroablation implement 21 and optical beacon 20 are in contact with the bone 55 of the lateral nasal wall 14. FIG. 5B depicts the further insertion of surgical probe shaft 16 towards the target posterior nasal nerve 8. The distal end 18 of probe shaft 16 follows the surgical plane 71 defined by the facial boundary between the mucosa 56 and the bone of the lateral nasal wall 14 as shown. The light 30 from optical beacon 20 trans-illuminates the mucosa 56 and can be visualized by endoscopic observation of the mucosal surface 57 providing the surgeon with a precise indication of the position of the distal end 18 of surgical probe 16 relative to the surrounding anatomical landmarks. The shape of distal end 18, and the flex characteristics of flexible segment 22 of probe shaft 16 are optimized to bluntly dissect along surgical plane 71 as distal end is advanced towards target posterior nasal nerve 8, as shown.

FIG. 5C depicts distal end 18 positioned immediately proximate to target posterior nasal nerve 8, which is co-sheathed with the sphenopalatine artery and vein. As the optical beacon 20 approaches the target posterior nasal nerve 8, the trans-illumination dims as the green light 30 is strongly absorbed by the hemoglobin in the blood flowing through the sphenopalatine artery and vein. In addition, as the optical beacon 20 approaches the target posterior nasal nerve 8, a portion of the light 30 escapes down the sphenopalatine foramen, instead of reflecting, off the bone 55 and towards the mucosal surface 57, this contributes to the dimming of the trans-illumination. The surgeon may determine that the distal end 18, and neuroablation implement 21 is in an optimal position for sub-mucosal neuroablation at the location of maximal dimming of the trans-illumination. The ideal zone of effect of neuroablation 69 is depicted as a sphere. The means of neuroablation may be a tissue freezing mechanism, a tissue heating and coagulation mechanism, or by sub-mucosal delivery of a neurolytic solution proximate to the target posterior nasal nerve 8 or its branches 10, 11 or 12. In addition, distal end 18 may comprise an ultrasonic. Doppler flow sensor, or an optical Doppler flow sensor to locate the sphenopalatine artery and vein in order to position distal end 18 into an optimal position for sub-mucosal neuroablation.

While the treatment is performed upon the targeted tissue with the neuroablation mechanism, the mucosa surrounding the region is ideally preserved. Hence, the neuroablation treatment may be controlled, modulated, or limited so as to treat the surrounding tissue immediately around the neuroablation implement 21 to a thickness of, e.g., 50-1000 microns.

Optionally, a thermally conductive substance such as a gel G may be placed upon the mucosal surface 57 in proximity to the probe shaft where the tissue is treated. The gel G may help to maintain the mucosal temperature near body temperature while the treatment occurs so as to preserve the mucosa. Moreover, the gel G may be deposited prior to or during the treatment by various mechanisms. Additionally, while the mucosal surface 57 directly above the treatment region may be coated with the gel G, other regions of the mucosal surface 57 may also be coated with the gel G as well to facilitate the dissipation of any heat transfer. Gel G can be preheated when a freezing method of ablation is used or pre cooled when a heating method of ablation is used, to more effectively protect the mucosal tissue.

Figure 5D:
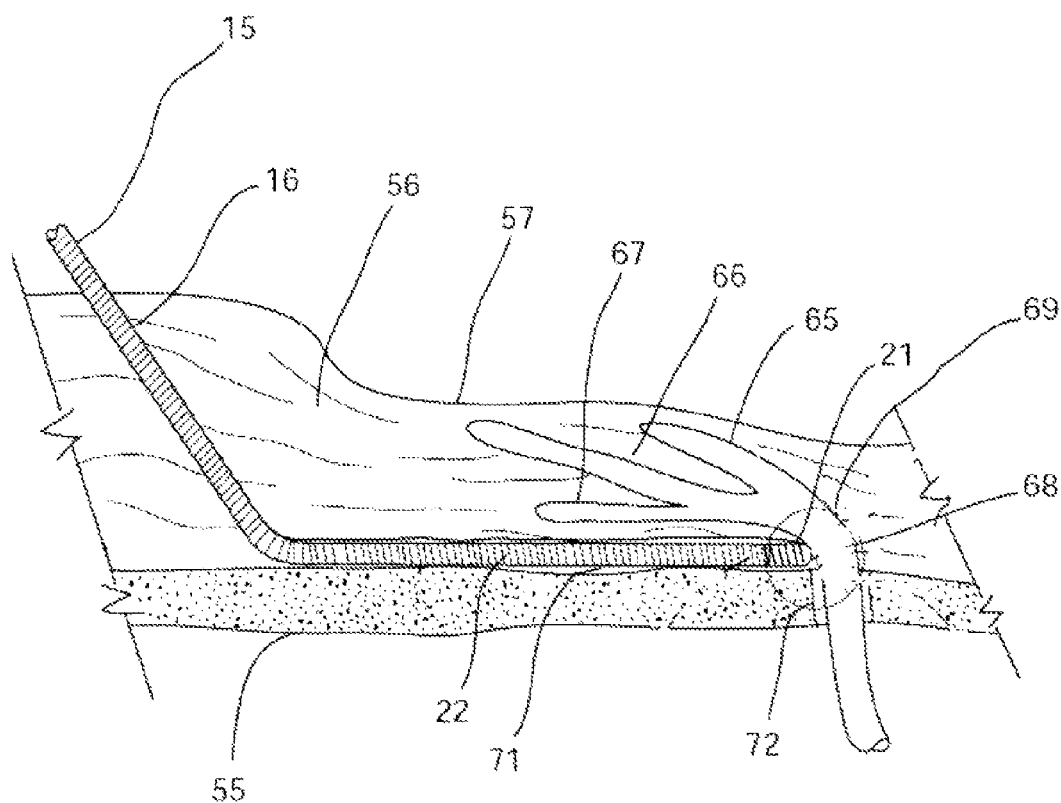
FIG. 5D is a cross section schematic illustration of the surgical probe shaft with the distal end coiled within the sub mucosal space.
Figure 5E:
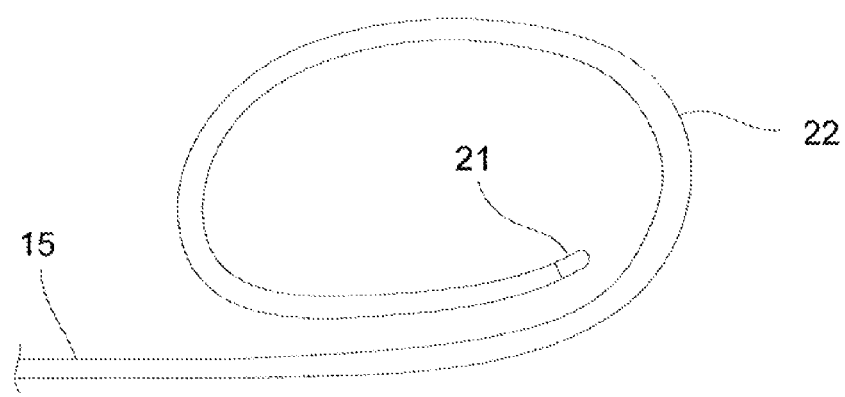
FIG. 5E is a top view of the coiled distal end of the shaft shown in FIG. 5D.

In yet another embodiment of the neuroablation probe 15, FIG. 5D illustrates a probe 15 having a flexible segment 22 which is sufficiently flexible to coil upon itself when deployed within the tissue. FIG. 5E shows a top view of the flexible segment 22 which may be coiled beneath the mucosal tissue so as to form a planar structure. The neuroablation implement 21 disposed near the distal end of flexible segment 22 may still be positioned in proximity to the targeted tissue but because of the formed planar configuration, the tissue immediately above and below the plane may be appropriate treated.

Figures 6A, 6B:
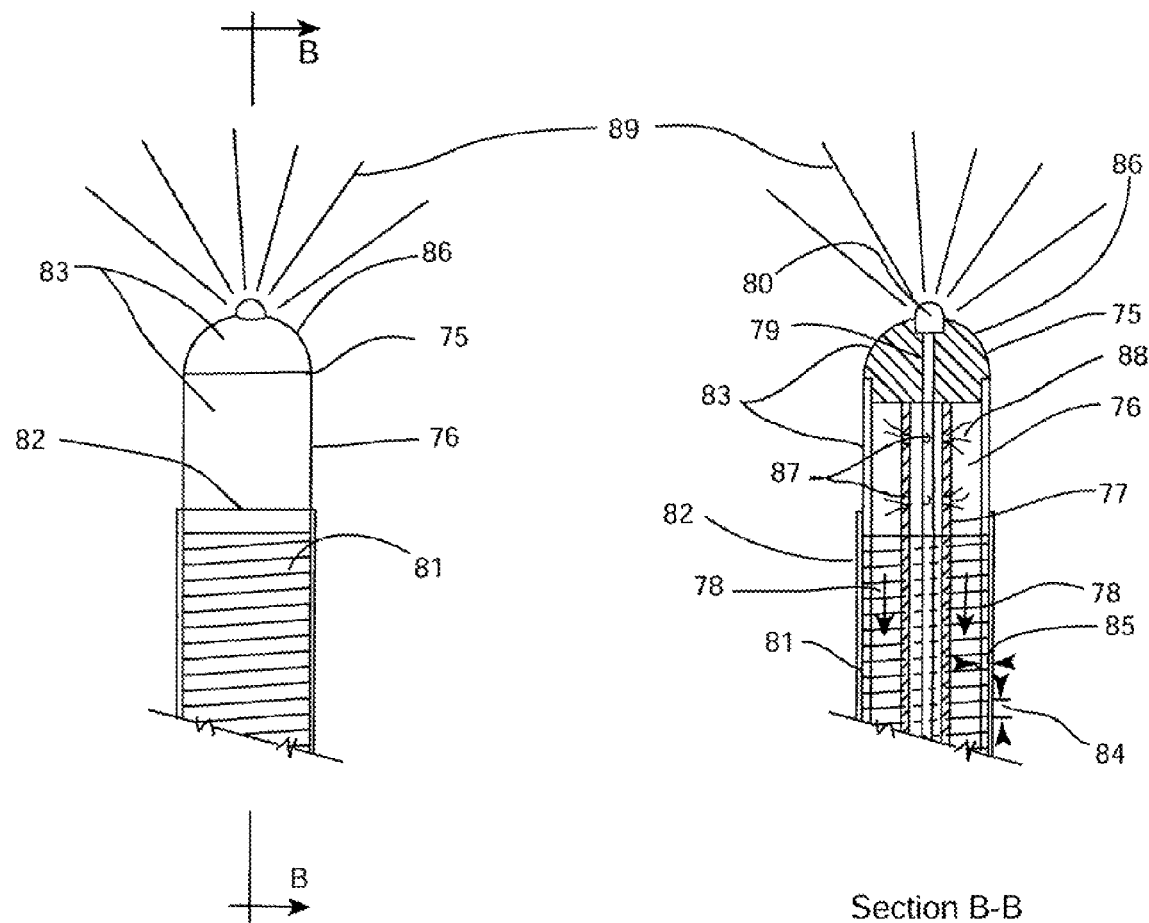
FIG. 6A is a schematic illustration of the distal end of a sub-mucosal neuroablation probe configured for tissue freezing.
FIG. 6B is a cross section schematic illustration of the sub-mucosal neuroablation probe of FIG. 6A.

FIG. 6A is a schematic illustration of the distal end 74 of surgical probe shaft 75 of sub-mucosal cryoablation probe 73. Sub-mucosal cryoablation probe 73 utilizes a tissue freezing neuroablation mechanism. FIG. 6B is a cross sectional schematic illustration of sub-mucosal cryoablation probe 73 taken at section "A-A" from FIG. 6A. Cryogen evaporation chamber 76 is disposed on the distal end 74 of flexible segment 90 of surgical probe shaft 75, as shown. Cryogen evaporation chamber 76 comprises evaporator cylinder 91, which is a hollow cylindrical structure that may be fabricated from stainless steel hypodermic tubing, which defines the lateral wail of evaporation chamber 76, and evaporation chamber cap 86, which defines the distal end of evaporation chamber 76. The proximal end of cryogen evaporation chamber 76 is open and in sealed fluidic communication with cryogen exhaust gas pathway 78, which is the central lumen of surgical probe shaft 75. Optical diffuser 80 is disposed at the distal tip of evaporation chamber cap 86 as shown. The distal end of optical fiber 79 is in an optical arrangement with optical diffuser 80 at its distal end, and the source of illumination at its proximal end, which may reside within the surgical hand piece, not shown. Optical diffuser 80 is configured to diffuse emitted light in a substantially uniform manner over a spherical arch between approximately 90 to 120 degrees. Cryogen delivery tube 77 is in fluidic communication with a liquid cryogen source, which may be disposed in the surgical hand piece, and the cryogen evaporation chamber 76, through liquid cryogen metering ports 87. Metering ports 87 are small fenestrations in the wall of liquid cryogen delivery tube 77, and are configured in size and quantity to meter liquid cryogen into the evaporation chamber 76 in a manner that ensures that the rate of liquid cryogen evaporation is sufficient to lower the temperature of the tissue freezing surface 83 sufficiently to freeze a large enough volume of tissue for effective neuroablation. The interior of liquid cryogen evaporation chamber 76 may comprise a liquid absorbing material configured to retain cryogen when in its liquid state, and release cryogen in its gaseous state to prevent liquid cryogen from exhausting down the cryogen gas exhaust path 78. Flexible segment 90 of probe shaft 75 comprises a tightly wound metal wire coil 81 with a major dimension 84 between approximately, e.g., 0.25 mm and 1.5 mm, and a minor dimension 85 between approximately, e.g., 0.10 mm and 0.40 mm. Wire coil 81 is wrapped with a polymeric liner 82 the entire length of flexible segment 90 to maintain wire coil 81 integrity, and to provide a fluid tight wall for the entire length of flexible segment 90. Optical fiber 79 may reside in a coaxial arrangement with liquid cryogen delivery tube 77 as shown, or may reside within cryogen gas exhaust path 78.

Figure 7A:
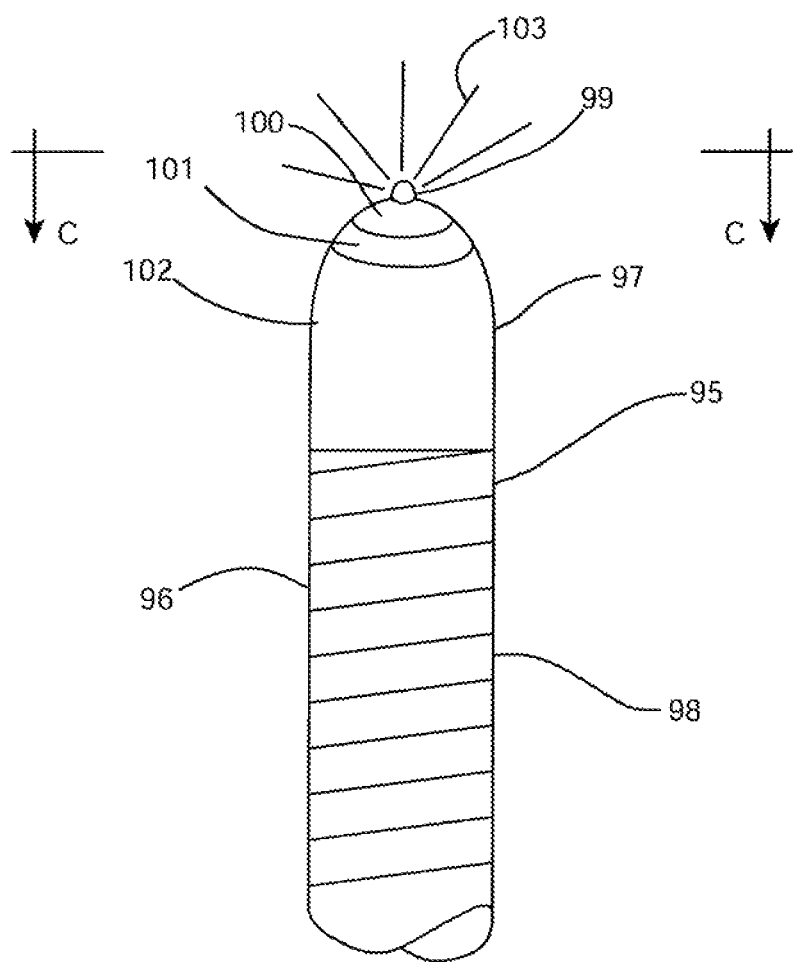
FIG. 7A is a schematic illustration of the distal end of a Rib-mucosal neuroablation probe configured for tissue heating by means of a bipolar radiofrequency (RF) energy electrode pair.
Figure 7B:
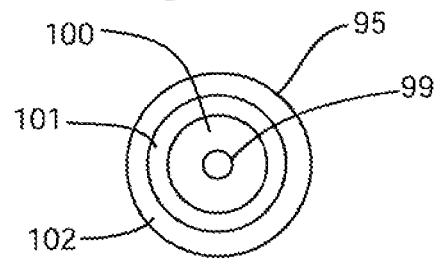
FIG. 7B is schematic end-view illustration of the sub-mucosal neuroablation probe of FIG. 7A.

FIG. 7A and FIG. 7B are schematic illustrations of the distal end 97 of bipolar RF sub-mucosal neuroablation probe 95, which is configured for sub-mucosal neuroablation by tissue heating and coagulation mechanism. Coagulation RF electrode 100 is disposed on the distal end 97 and surrounds optical beacon 99. Neutral RF electrode 102 is disposed proximal to coagulation RF electrode 100, and is electrically isolated from coagulation RF electrode 100 by electrical isolator 101. Coagulation RF electrode 100 is connected to one pole of an RF energy generator, not shown, with a wire, where the RF energy generator may he disposed within the surgical hand piece, not shown. Neutral RF electrode 102 is connected to the second pole of the RF generator with a wire. The surface area of neutral RF electrode 102 is between approximately, e.g., 3 to 10 times greater than the surface area of the coagulation RF electrode 100. During use RF current flows between coagulation RF electrode 100, and Neutral RF electrode 102, through the tissue contacting the two electrodes 100 and 102. The difference in surface area between the two electrodes 100 and 102 results in a substantially higher RF current density at the surface of the coagulation RF electrode 100, resulting in a concentration of joule effect heating at the surface of the coagulation RF electrode 100. The level of Joule effect heating at the surface of the neutral RF 102 electrode is insufficient to raise the temperature of the contacting tissue to level that result in thermal injury. Other embodiments that utilize a tissue heating and coagulation as a neuroablation mechanism remain within the scope of this invention.

Figure 8A:
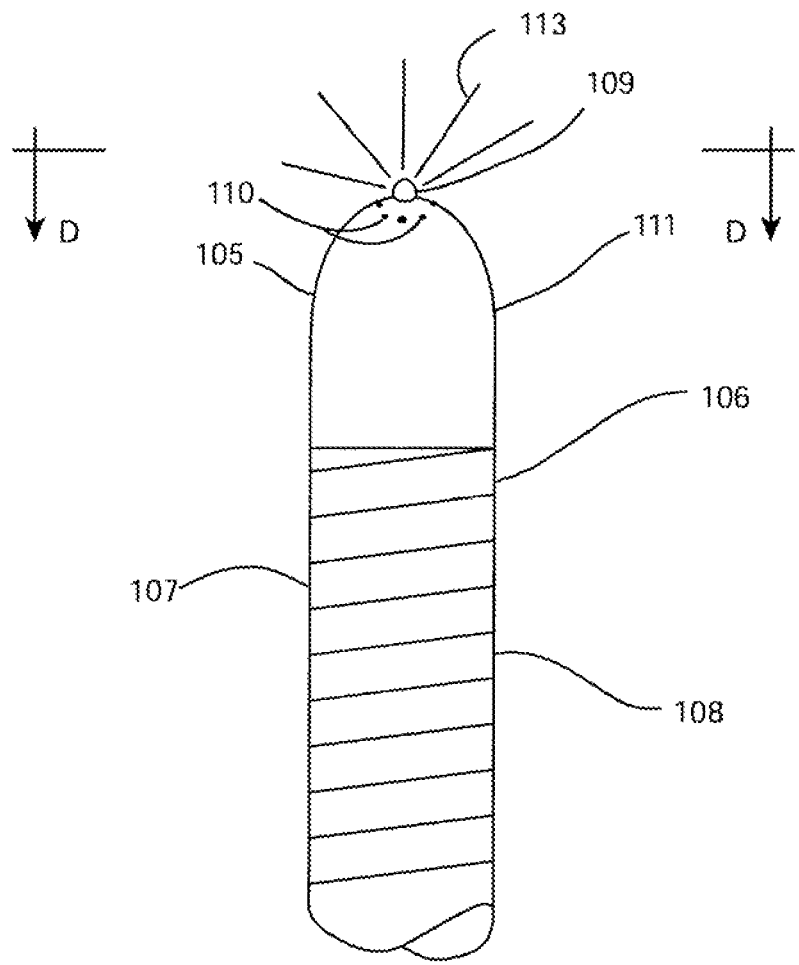
FIG. 8A is a schematic illustration of a sub-mucosal neuroablation probe configured for sub-mucosal delivery of a neurolytic solution.
Figure 8B:
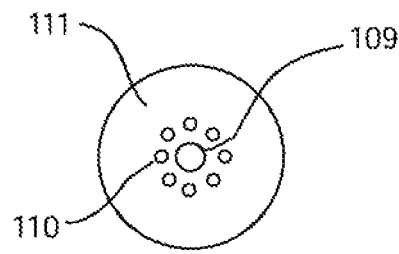
FIG. 8B is a schematic end-view illustration of the sub-mucosal neuroablation probe of FIG. 8A.

FIG. 8A and FIG. 8B are schematic illustrations of the distal end 106 of sub-mucosal neurolytic solution delivery (SMNSD) probe 105, which is configured for sub-mucosal delivery of a neurolytic solution for the treatment of rhinitis. SMNSD probe 105 comprises surgical probe shall 107, and a surgical probe hand piece not shown. Surgical probe shall 107 comprises distal end 106 and a proximal end not shown. Distal tip 111 is disposed on the distal end of flexible segment 108. Optical beacon 109 is disposed at the distal end of distal tip 111 as shown and previously described. Distal tip 111 comprises at least one fluid port 110 disposed in the vicinity of the distal end 106 in an arraignment that may be similar to that depicted. At least one fluid port 110 is in fluidic communication with a reservoir, not shown comprising a neurolytic solution. The reservoir may be disposed on or within the surgical hand piece, or may comprise a syringe in fluidic communication with the hand piece and fluid port(s) 110. The surgical hand piece may comprise a means for transferring a portion of the neurolytic solution front the reservoir into the sub-mucosal tissue space about distal tip 111 during use. The neurolytic solution may comprise a neurotoxic agent, a sympatholytic agent, or a sclerosing agent. A neurotoxic agent may be botulinum toxin, β-Bunarotoxin, tetnus toxin, α-Latrotoxin or another neurotoxin. A sympatholytic agent may be Guanethidine, Guanacline, Bretylium Tosylate, or another sympatholytic agent. A sclerosing agent may be ethanol, phenol, a hypertonic solution or another sclerosing agent. The neurolytic solution may have a low viscosity similar to water, or neurolytic solution may have a high viscosity and be in the form of a gel. The gel functions to prevent migration of the neurolytic solution from the target space.

Figure 9:
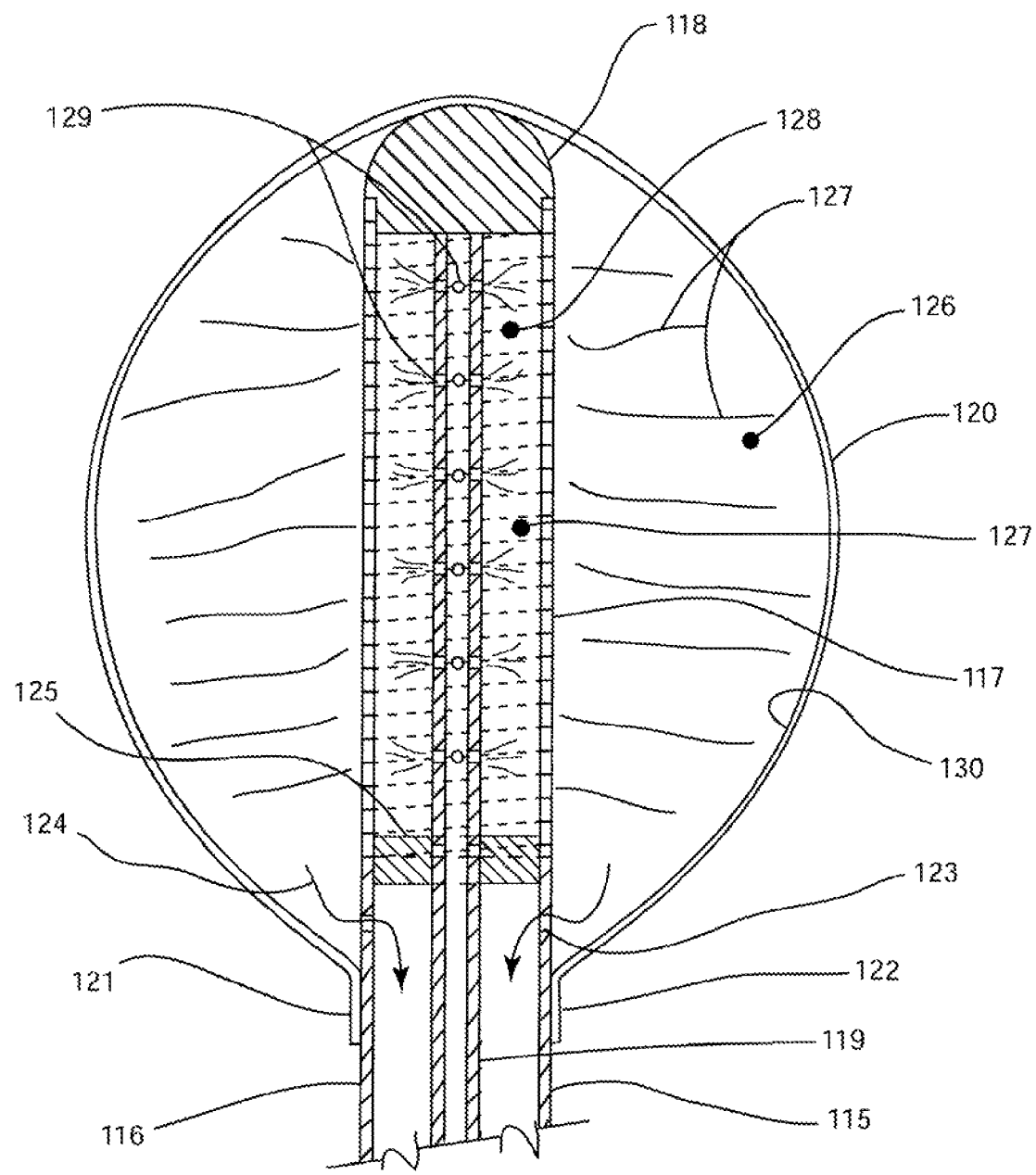
FIG. 9 is a cross sectional schematic illustration of a sub-mucosal neuroablation probe configured for tissue freezing using an expandable structure as a cryogen evaporation chamber, which also functions as an endoscopic visualization aid.

FIG. 9 is a cross sectional schematic illustration of the distal end of generic sub-mucosal neuroablation probe 115 comprising a neuroablation implement comprising an expandable evaporation chamber 120 configured for tissue freezing, which also functions as an expandable endoscopic visual aid. Depicted is the distal end of probe shaft 116, wire coil structure 117, end cap 118, liquid cryogen supply line 119, expandable membranous structure 120, in its expanded state, ostium 121, adhesive bond 122 between ostium 121 and probe shaft 116, cryogen gas exhaust vent 123, exhaust gas flow path 124, pressure bulkhead 125, liquid cryogen evaporation chamber 126, and liquid cryogen 127. Liquid cryogen chamber 128 is defined by spring coil 117, end cap 118, and pressure bulkhead 125. Liquid cryogen 127 enters liquid cryogen chamber 128 through liquid cryogen supply line 119, and through liquid cryogen ports 129. Wire coil 117 is configured to meter liquid cryogen 127 from liquid cryogen chamber 128 into liquid cryogen evaporation chamber 126 in a manner that sprays liquid cryogen 127 in the direction of interior surface 130 of expandable membranous structure 120 so that the liquid cryogen rapidly evaporates upon contact with inner surface 130. A perforated polymeric liner, not shown, disposed upon wire coil 117 may be used to provide proper metering and spatial distribution of liquid cryogen 127. Sub-mucosal neuroablation probe 115 is configured so expandable membranous structure 120 expands to a predetermined size and shape in response to liquid cryogen evaporation within. Sub-mucosal neuroablation probe 115 is also configured with a means for the user to expand the membranous structure 120 independently from liquid cryogen 127 evaporation in a manner that allows the expandable membranous structure 120 to function as an endoscopic visualization aid as previously described. Sub-mucosal neuroablation probe 115 is configured such that the outer surface of expandable membranous structure 120 will be between approximately, e.g. −20 Deg. C to −50 Deg. C. during cryogen 127 evaporation within. Expandable membranous structure 120 is a hollow bulbous structure in its expanded state, and comprises a single ostium 121 configured for adhesive bonding to distal end of probe shaft 116 using adhesive bond 122. Cryogen exhaust vent 123 comprises at least one fenestration in distal end of probe shaft 116, which is in fluidic communication with a proximal vent port, not shown, and the room. A pressure relief valve, not shown, may be disposed in the fluid path between the interior of expandable membranous structure 120 and the room to control the pressure within expandable membranous structure 120. the degree of expansion during liquid cryogen 127 evaporation.

The applications of the disclosed invention discussed above are not limited to certain treatments or regions of the body, but may include any number of other treatments and areas of the body. Modifications of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A method for treating rhinitis of a patient, the method comprising:
    visualizing a tissue region of a lateral nasal wall located within a nasal cavity of the patient;
    inserting a distal end of a surgical probe into a sub-mucosal space of the lateral nasal wall of the patient, the surgical probe comprising a surgical probe shaft with a proximal end and the distal end, a handle coupled to the proximal end, a cryo-ablation element disposed on the distal end, and a position indicator disposed in the vicinity of the distal end;
    advancing the distal end of the surgical probe shaft within the lateral nasal wall tissue region and towards at least one posterior nasal nerve associated with the lateral nasal wall tissue region while visually tracking a position of the distal end with the position indicator; and
    cryogenically ablating the at least one posterior nasal nerve with the cryo-ablation element to reduce at least one symptom of rhinitis.

2. The method of claim 1 further comprising detecting or quantifying an arterial blood flow within the lateral nasal wall region with a sensor prior to ablating the at least one posterior nasal nerve.

3. The method of claim 2 wherein the sensor comprises an ultrasonic or optical sensor.

4. The method of claim 1 wherein cryogenically ablating the at least one posterior nasal nerve comprises delivering a cryogenic fluid into the cryo-ablation element from a cryogenic fluid source fluidly connected to the cryo-ablation element.

5. The method of claim 4 wherein the cryo-ablation element comprises an expandable membranous structure such that the expandable structure is inflated from a deflated configuration to an expanded configuration in contact against the tissue region of the lateral nasal wall.

6. The method of claim 1 wherein cryogenically ablating the at least one posterior nasal nerve comprises freezing via a Joule-Thompson gas expansion mechanism.

7. The method of claim 1 wherein the distal end of the surgical probe is inserted into the sub-mucosal space at a position substantially anterior to a middle nasal turbinate or an inferior nasal turbinate of the patient.

8. The method of claim 1 wherein the distal end of the surgical probe is inserted into the sub-mucosal space substantially in between a middle nasal turbinate and an inferior nasal turbinate of the patient.

9. The method of claim 1 wherein the distal end of the surgical probe is inserted into the sub-mucosal space in a vicinity of a cul de sac defined by a tail of a middle nasal turbinate, lateral nasal wall, and inferior nasal turbinate of the patient.

10. The method of claim 1 wherein inserting the distal end of the surgical probe comprises advancing the distal end of the probe shaft to a position proximate of the at least one posterior nasal nerve along a surgical plane defined by a bone of the lateral nasal wall and a nasal mucosa.

11. The method of claim 1 wherein inserting the distal end of the surgical probe comprises advancing the distal end of the probe shaft to a position proximate to the at least one posterior nasal nerve while avoiding damage to arteries, veins, and non-target nerves.

12. The method of claim 1 further comprising protecting a superficial mucosal tissue from injury while cryogenically ablating at least one posterior nasal nerve.

13. The method of claim 12 wherein protecting the superficial mucosal tissue comprises warming the superficial mucosal tissue.

14. The method of claim 1 wherein cryogenically ablating at least one posterior nasal nerve comprises ablating a surrounding region of tissue to a depth of 50-1000 microns.

15. The method of claim 1, wherein the position indicator comprises an optical beacon, and wherein visually tracking the position of the distal end of the probe shaft comprises trans-illuminating the optical beacon through mucosa.

16. The method of claim 15, wherein the optical beacon is configured to emit light having a wavelength suitable for optical absorption by hemoglobin.

17. The method of claim 15, wherein the optical beacon is configured to emit light having a wavelength in a visible light spectrum.

18. The method of claim 17, wherein the optical beacon is configured to emit light having a wavelength substantially in a green segment of the visible light spectrum.

19. The method of claim 15, further comprising adjusting a brightness of the optical beacon prior to cryogenically ablating at least one posterior nasal nerve.

20. The method of claim 1, wherein the position indicator comprises an expandable structure, and wherein visually tracking the position of the distal end of the probe comprises expanding the expandable structure so as to displace mucosal tissue overlying the distal end of the probe.

21. The method of claim 20, wherein the cryo-ablation element comprises the expandable structure.

22. The method of claim 21, wherein cryogenically ablating the at least one posterior nasal nerve comprises introducing liquid cryogen into the expandable structure so as to cryogenically ablate the at least one posterior nasal nerve.

23. The method of claim 20, wherein visually tracking the position of the distal end of the probe comprises endoscopically visualizing a displacement of mucosal tissue overlying the distal end of the probe.

* * * * *